US007106866B2

(12) United States Patent
Astorino et al.

(10) Patent No.: US 7,106,866 B2
(45) Date of Patent: Sep. 12, 2006

(54) ACTIVE NOISE CANCELLATION STABILITY SOLUTION

(75) Inventors: John F. Astorino, Livonia, MI (US); Ian R. McLean, Chatham (CA); Trevor Laak, Oregon, WI (US)

(73) Assignee: Siemens VDo Automotive, Inc., Chatham (CA)

(*) Notice: Subject to any disclaimer, the term of this patent is extended or adjusted under 35 U.S.C. 154(b) by 889 days.

(21) Appl. No.: 09/828,021

(22) Filed: Apr. 6, 2001

(65) Prior Publication Data

US 2001/0036281 A1 Nov. 1, 2001

Related U.S. Application Data

(60) Provisional application No. 60/195,026, filed on Apr. 6, 2000.

(51) Int. Cl.
*A61F 11/06* (2006.01)
*H04B 1/00* (2006.01)

(52) U.S. Cl. .................... 381/71.4; 381/86; 381/71.11; 381/71.12

(58) Field of Classification Search ............... 381/71.1, 381/71.4, 71.5
See application file for complete search history.

(56) References Cited

U.S. PATENT DOCUMENTS 4,506,380 A * 3/1985 Matsui ...................... 381/71.9
5,359,662 A 10/1994 Yuan et al.
5,386,477 A 1/1995 Popovich et al.
5,418,873 A 5/1995 Eriksson
5,420,932 A 5/1995 Goodman
5,557,682 A 9/1996 Warner et al.
5,561,598 A 10/1996 Nowak et al.
5,570,425 A 10/1996 Goodman et al.
5,571,239 A 11/1996 Kameda et al.
5,581,619 A * 12/1996 Shibata et al. ............. 381/71.4
5,586,189 A 12/1996 Allie et al.
5,586,190 A 12/1996 Trantow et al.
5,590,205 A 12/1996 Popovich
5,602,928 A 2/1997 Eriksson et al.
5,602,929 A 2/1997 Popovich
5,621,803 A 4/1997 Laak
5,627,747 A 5/1997 Melton et al.
5,633,795 A 5/1997 Popovich
5,680,337 A 10/1997 Pedersen et al.
5,690,321 A 11/1997 Seni et al. ............. 267/140.14
5,701,350 A 12/1997 Popovich (Continued)

FOREIGN PATENT DOCUMENTS

EP 0 611 089 A2 8/1994

(Continued)

OTHER PUBLICATIONS

J. Acoust. Soc. Am 86(2), Aug. 1989; Analysis of a hybrid noise control system for a duct, M.L. Munjal and L.J. Eriksson.

(Continued)

*Primary Examiner*—Laura A. Grier

(57) ABSTRACT

The method of noise attenuation comprises the steps of generating a noise canceling signal, sensing for an system condition, and ceasing the generation of the noise canceling based upon the system condition. This method is embodied in a system that includes an air induction body, a speaker in proximity to the air induction body, a sensor for sensing a system condition, and a control unit with a noise cancellation feature. The control unit is in communication with both the speaker and the sensor. Based upon the sensed system condition, the control unit may disable the noise cancellation feature.

11 Claims, 2 Drawing Sheets

U.S. PATENT DOCUMENTS

| | | | | |
|---|---|---|---|---|
| 5,706,344 | A | 1/1998 | Finn | |
| 5,710,822 | A | 1/1998 | Steenhagen et al. | |
| 5,715,320 | A | 2/1998 | Allie et al. | |
| 5,828,759 | A | 10/1998 | Everingham | |
| 5,963,651 | A | 10/1999 | Van Veen et al. | |
| 6,084,971 | A | 7/2000 | McLean | |
| 6,094,601 | A | 7/2000 | Popovich | |
| 2001/0046300 | A1 * | 11/2001 | McLean | 381/71.4 |

FOREIGN PATENT DOCUMENTS

| | | | |
|---|---|---|---|
| EP | 0 611 089 | A3 | 8/1994 |
| EP | 0 661 807 | A2 | 7/1995 |
| EP | 0 684 594 | A2 | 11/1995 |
| EP | 0 721 178 | A2 | 7/1996 |
| EP | 0 721 179 | A2 | 7/1996 |
| EP | 0 759 606 | A2 | 2/1997 |
| EP | 0 661 807 | A3 | 4/1997 |
| EP | 0 773 531 | A2 | 5/1997 |
| EP | 0 684 594 | A3 | 10/1997 |
| EP | 0 721 179 | A3 | 5/1998 |
| EP | 0 721 178 | A3 | 12/1998 |
| EP | 0 759 606 | A3 | 12/1998 |
| EP | 0 773 531 | A3 | 12/1998 |
| EP | 0 884 471 | A2 | 12/1998 |
| EP | 0 903 726 | A2 | 3/1999 |
| EP | 0 932 142 | A2 | 7/1999 |
| EP | 0 949 795 | A2 | 10/1999 |
| EP | 0 932 142 | A3 | 3/2000 |
| EP | 0 611 089 | B1 | 6/2000 |
| JP | 7-56582 | | 3/1995 |
| JP | 8-46489 | | 2/1996 |
| JP | 2000267674 | | 9/2000 |
| JP | 2001282253 | | 10/2001 |
| WO | WO 99/17275 | | 4/1999 |

OTHER PUBLICATIONS

J. Acoust. Soc. Am. 85(2), Feb. 1989; Use of random noise for on-line transducer modeling in an adaptive active attenuation system, L.J. Eriksson and M.C. Allie.

EP Search Report, Application No. EP01108288, date of completion Sep. 8, 2004.

* cited by examiner

ACTIVE NOISE CANCELLATION STABILITY SOLUTION

This application claims priority to Provisional Patent Application Ser. No. 60/195,026 filed Apr. 6, 2000.

BACKGROUND OF THE INVENTION

This invention relates to an active method and system for controlling automotive induction noise.

Manufacturers have employed active and passive methods to reduce engine noise within the passenger compartment. Such noise frequently emanates from the engine, travels through the air induction system and emanates out of the mouth of the air intake into the passenger compartment. Efforts have been made to reduce the amount of engine noise traveling through the air induction system. These efforts include the use of both passive devices such as expansion chambers and Helmholtz resonators and active devices involving anti-noise generators.

Active systems use a speaker to create a canceling sound that attenuates engine noise. The sound created is out of phase with the engine noise and combines with this noise to result in its reduction. Generally, this sound is generated in proximity to the mouth of the air induction system. In one such system, a control unit, such as a digital signal processor, obtains data from the vehicle engine, creates a predictive model of engine noise, and thereby generates the appropriate cancellation signal based on the results of this model. This signal is then transmitted to the speaker, which transforms this signal into a canceling sound. Because the control unit may not perfectly model engine noise, an error microphone is placed in proximity to the mouth of the air induction system to determine if engine noise need be further attenuated.

At times of low engine load, such as when the vehicle is cruising or idling, such a system may experience a condition of low engine noise to background noise. As a consequence, rather than quieting noise in the passenger compartment, the system generates a high pitch sound. This sound is undesirable.

A need therefore exists to prevent the generation of this undesirable tone by a noise cancellation system.

SUMMARY OF THE INVENTION

The invention concerns a method and system of controlling noise attenuation. As known, to attenuate engine noise, a noise canceling signal is generated by a computer that emits this signal through a speaker in proximity to the source of the noise. When system conditions are detected that may result in the generation of an undesirable noise by the noise attenuation system, the noise cancellation feature is temporarily disabled. In this way, the method and system avoid the creation of an undesirable noise that is frequently generated by noise attenuation systems at times of low engine load.

The system condition may be related to engine noise, background sound, or the relationship of engine noise to background sound. For example, if engine noise is low relative to background sound, the noise attenuation system is susceptible to the creation of an unwanted high pitch sound. In this situation, the invention temporarily disables the system to avoid the generation of this sound.

Additionally, the sensed system condition may also relate to the position of the throttle. When the engine is at low load conditions, such as at idle or at cruising speed, there is little need for noise attenuation. However, under certain circumstances, the system may create an unwanted noise as a consequence of system error. If the system detects such a noise when the throttle is moved toward closed, the system disables the noise attenuation system.

The noise attenuation system is only temporarily disabled. When the system senses a change from the system condition that may result in the generation of an unwanted noise, the system is enabled to once again commence noise attenuation. The system may keep a record of the disabling of the noise attenuation system based on a system condition. Such a record keeps track of the number of system errors that result or may result in the generation of unwanted noise. In the event that the number of disables exceeds a preset level, then the noise attenuation system is disabled again and an error message is issued. The system may wait a set period of time before again commencing the noise attenuation process to permit system conditions to change.

In an air induction system, the noise attenuation system comprises an air induction body and a speaker in proximity to the air induction body. A sensor detects the system condition and communicates with a control unit that has a noise cancellation feature. In the event system condition that may result in the generation of unwanted noise is detected, the noise cancellation feature is disabled.

BRIEF DESCRIPTION OF THE DRAWINGS

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
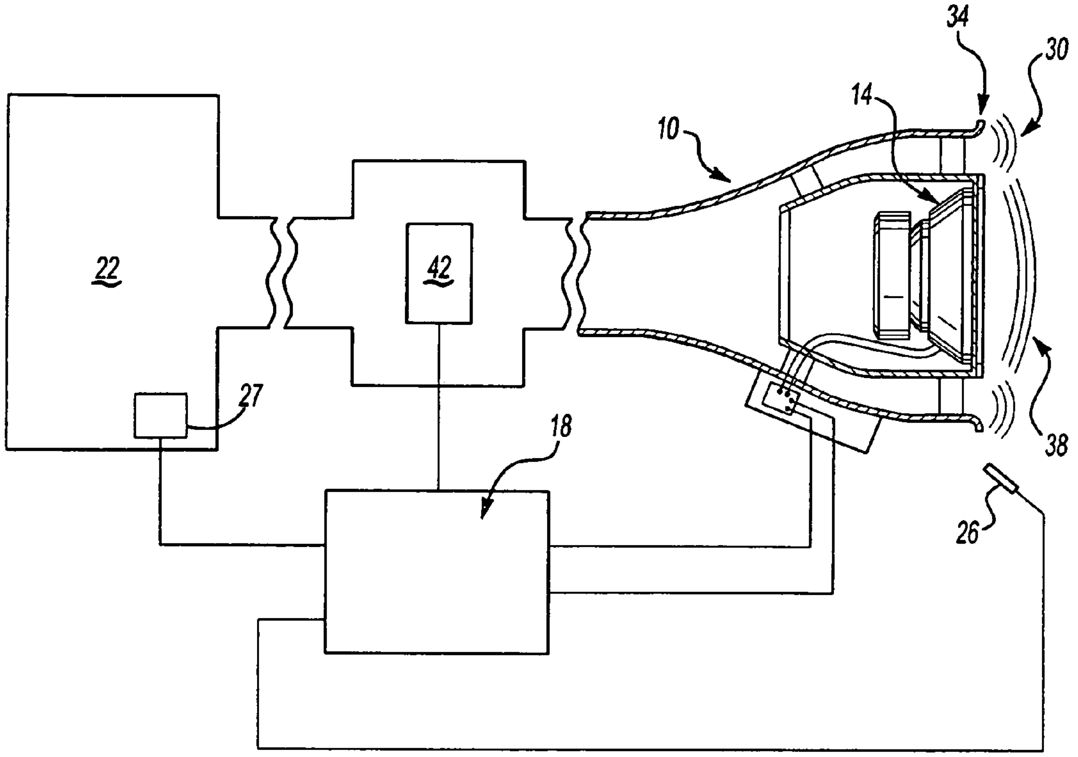
FIG. 1 shows a schematic view of the system employing the embodiment of the invention.

FIG. 1 illustrates the method and system of noise attenuation of an embodiment of the invention. Pictured schematically are air induction body 10 and speaker 14, preferably disposed in air induction body 10, control unit 18, engine 22, and sensor 26, here an error microphone, and reference sensor 27, such as an engine tachometer. Engine noise 30 from engine 22 travels through air induction body 10 out of mouth 34 of air induction body 10. As known, during normal operation, control unit 18 has a noise cancellation feature that generates a noise canceling signal 38 through speaker 14. Because noise canceling signal 38 is out of phase with engine noise 30, both noise canceling signal 38 and engine noise 30 are thereby attenuated.

The invention includes at least one sensor 26 for sensing a system condition, which is in communication with control unit 18. When a predetermined system condition is detected by sensor 26, the noise cancellation feature of control unit 18 is disabled. Preferably, the predetermined system condition is based on engine noise level received by sensor 26 (an error microphone), background noise level received by sensor 26, or preferably a relationship between engine noise level and background noise level. The system conditions may be factors likely to result in the generation of unwanted noise from the noise attenuation system without the disabling of the system. For example, a low engine noise level to background noise level would indicate a situation where unwanted noise may be generated. In this situation as well as other circumstances, control unit 18 disables the noise attenuation feature to prevent the generation of unwanted noise.

Another system condition reviewed by the system is the position of the vehicle throttle as detected by a throttle position sensor as known. Sensor 42 detects the position of the throttle blade and communicates this position to control unit 18. If sensor 26, here an error microphone, detects a high pitch sound while sensor 42 detects the throttle position to be moved toward a closed position, then control unit 18 deduces that the sound is unwanted noise from the system and shuts off its noise attenuation feature, thereby eliminating the high pitch sound.

Essentially, the method of noise attenuation involves generating a noise canceling signal, sensing for the system condition, and ceasing the generation of the noise canceling signal based upon the system condition as described above. The method may further involve sensing for a change in a system condition. When a change from the system condition that creates the unwanted noise is detected, control unit 18 may again commence noise attenuation by generating another noise canceling signal. Control unit 18 may farther record the cessation of the generation of the noise canceling signal based upon the system condition. In other words, each cessation may be considered a system error or malfunction. In this way, if the number of errors or malfunctions exceeds a preset level, then control unit 18 deduces a system problem and ceases noise attenuation for a predetermined amount of time to permit systems conditions to possibly change to where noise attenuation may proceed without error and undesirable noise. Control unit 18 may issue an error message to the driver as well. After a predetermined amount of time, the system once again commences noise attenuation. In the event errors persist, then control unit 18 may permanently disable noise attenuation until the system is serviced.

Figure 2:
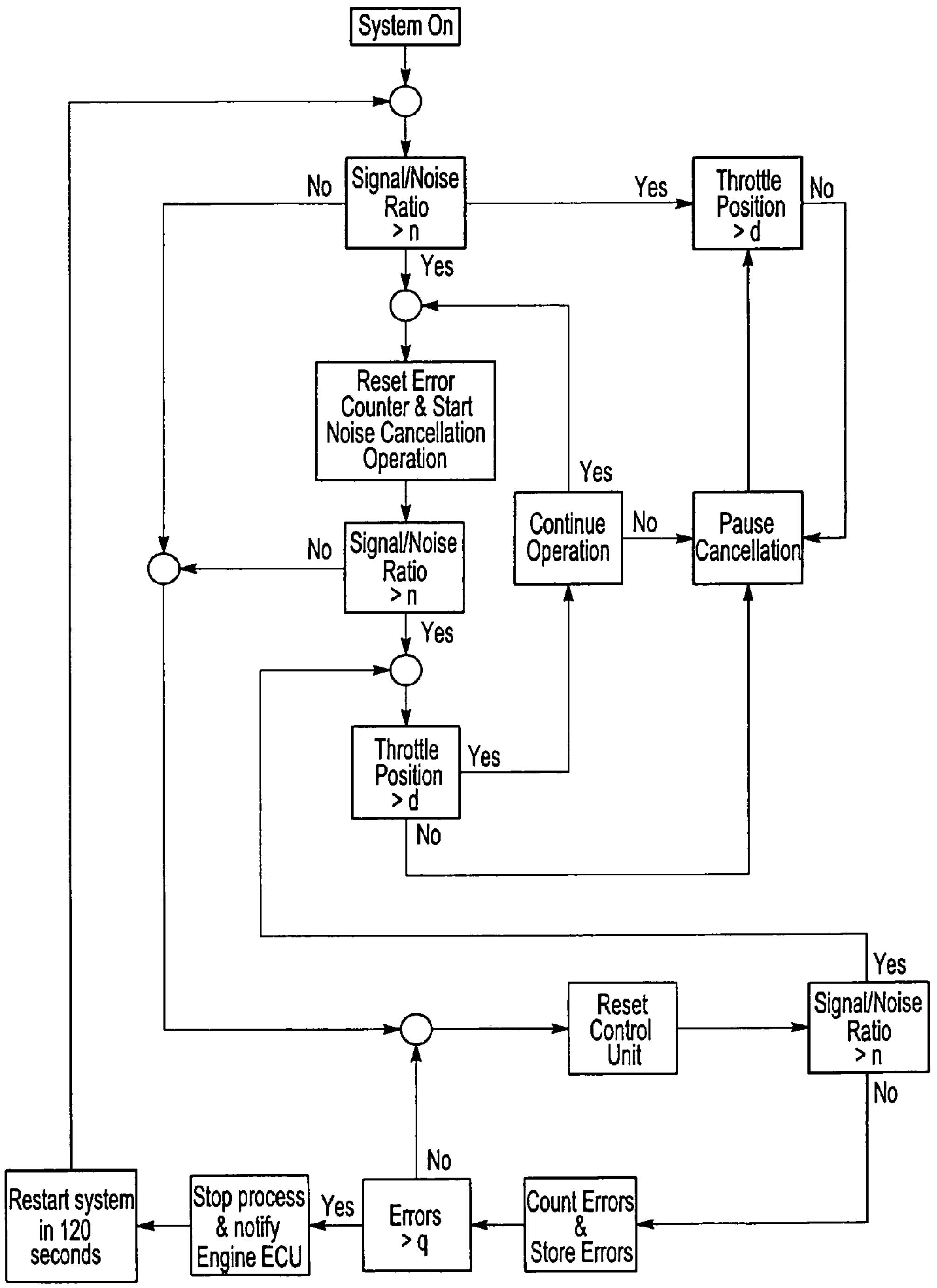
FIG. 2 shows a flowchart of an embodiment of the invention.

FIG. 2 is a flowchart of an embodiment of the above described method and system. When the system is "on", control unit 18 checks sensor 26 to determine whether the engine noise 30 to background noise ratio is above a predetermined level (n) to avoid generation of unwanted high pitch noise. If so, then normal operation of noise attenuation takes place and, as explained below, error counter is reset. As mentioned above, rather then this ratio, other system conditions can be used.

Control unit 18 again checks sensor 26 to review the current engine noise 30 to background noise ratio following noise attenuation. If this ratio is greater than "n," then control unit 18 checks sensor 42 to determine throttle position. If throttle position is open over a predetermined amount (d) as sensed by a throttle position sensor as known in the art, control unit 18 proceeds to determine whether control unit 18 need continue operation. If yes, then control unit 18 loops back to its noise attenuation routine to thereby attenuate engine noise. If throttle position is not open over "d," then control unit 18 pauses noise attenuation. Attenuation is paused until throttle is once again open as detected. When throttle is opened, then control unit 18 loops back to its noise attenuation routine.

If control unit 18 determines that the ratio between engine noise 30 and background noise is less than a predetermined level n for normal operation of noise attenuation, then control unit 18 resets to clear any system problem and checks again the ratio of engine noise 30 to background noise. If the ratio is sufficiently high, then control unit 18 checks the throttle position as shown. On the other hand, if the ratio is below a predetermined level n, then the error is counted and recorded. In the event that the number of errors exceeds a preset limit (q) as determined, then control unit 18 stops the noise attenuation process and notifies the engine computer of the error. Control unit 18 restarts, however, after a predetermined time period, in one example 120 seconds, to give the opportunity for the error to clear itself. After this period, control unit 18 recommences the process.

As known, control unit 18 employs a predictive model of engine noise, which is based on certain assumptions of the ambient environment, including air pressure, air temperature, and humidity about the engine compartment. When the environmental assumptions are incorrect, control unit 18 may generate a less than optimal noise cancellation signal and even create an undesirable high pitch noise. As more fully disclosed in pending U.S. patent application Ser. No. 09/827,794 filed on the same day of this application, which is hereby incorporated by reference, the invention may be used in conjunction with the method of noise attenuation whereby control unit 18 recalibrates based on new environmental conditions rather than assumed environmental conditions. In such an embodiment, the method of noise attenuation involves generating a noise canceling signal from control unit 18 based on an environmental assumption, sensing a system condition, ceasing the generation of the noise canceling signal based on the system condition, and recalibrating based on changed environmental conditions. The changed environmental conditions may be detected by comparing a test sound wave from speaker with the assumed model of the sound wave stored by the system. Differences between the sound waves may then result in recalibration. This method thereby permits control unit 18 to adjust its model of engine noise based on environmental conditions at a point where control unit 18 is not preoccupied with noise attenuation. More importantly, this method allows control unit to recalibrate and consequently avoid the generation of the unwanted noise.

The aforementioned description is exemplary rather then limiting. Many modifications and variations of the present invention are possible in light of the above teachings. The preferred embodiments of this invention have been disclosed. However, one of ordinary skill in the art would recognize that certain modifications would come within the scope of this invention. Hence, within the scope of the appended claims, the invention may be practiced otherwise than as specifically described. For this reason the following claims should be studied to determine the true scope and content of this invention.

What is claimed is:

1. A method of noise attenuation comprising the steps of:
generating an active noise canceling signal;
sensing engine noise;
sensing background sound;
comparing engine noise to background sound;
sensing a throttle position; and
ceasing the generation of the an active noise canceling signal based upon the throttle position and the comparing of engine noise to background sound.

2. The method of claim 1 wherein the engine noise and the background sound are related by a ratio.

3. The method of claim 2 wherein the ceasing of the generation of the an active noise cancelling is conditioned upon the ratio being greater than a predetermined level and the throttle position being less open than a predetermined position.

4. The method of claim 3 including the step of generating the an active noise cancelling signal when the throttle position is greater than the predetermined position.

5. The method of claim 1 wherein ceasing occurs when the throttle position is less open than a predetermined position.

6. A method of noise attenuation comprising the steps of:
generating an active noise canceling signal;
sensing engine noise;
sensing background sound;
comparing the engine noise to the background sound;
ceasing the generation of the an active noise canceling signal based upon the comparing of the engine noise to the background sound.

7. The method of claim 6 wherein the comparing of the engine noise to the background sound comprises a ratio of the engine noise to background sound.

8. The method of claim 7 wherein ceasing the generation of the an active noise cancelling signal is conditional upon the ratio being below a predetermined level.

9. The method of claim 8 further including the step of generating the an active noise canceling signal when the ratio exceeds the predetermined level.

10. The method of claim 8 further including the step of recording when the ratio is below the predetermined level.

11. The method of claim 10 wherein ceasing the generation of the an active noise cancelling signal is conditioned upon a predetermined number of instances of the recording number of the ratio between the predetermined level.

* * * * *